United States Patent [19]

Oxenius et al.

[11] Patent Number: 4,874,847
[45] Date of Patent: Oct. 17, 1989

[54] PROCESS FOR THE DIAZOTISATION OF PRIMARY AROMATIC AMINES WHICH ARE SPARINGLY SOLUBLE IN WATER

[75] Inventors: Rüdiger Oxenius, Rheinfelden, Fed. Rep. of Germany; Ernst Bürgi, Dornach, Switzerland; Arnold Vladimir, Basel, Switzerland; Ferenc Rakoczi, Zurich, Switzerland

[73] Assignee: Ciba-Geigy Corporation, Ardsley, N.Y.

[21] Appl. No.: 136,530

[22] Filed: Dec. 22, 1987

Related U.S. Application Data

[63] Continuation of Ser. No. 803,710, Dec. 2, 1985, abandoned.

[30] Foreign Application Priority Data

Dec. 6, 1984 [CH] Switzerland ............... 5825/84

[51] Int. Cl.$^4$ ........................... C07C 113/04
[52] U.S. Cl. ..................... 534/565; 534/558
[58] Field of Search ......................... 534/565

[56] References Cited

U.S. PATENT DOCUMENTS

| | | | |
|---|---|---|---|
| 3,117,954 | 1/1964 | Hupfer | 534/565 |
| 3,423,391 | 1/1969 | Kindler et al. | 534/565 |
| 4,083,846 | 4/1978 | Leverenz | 534/565 X |
| 4,234,478 | 11/1980 | Atherton et al. | 534/565 X |
| 4,246,171 | 1/1981 | Hamilton et al. | 534/565 |
| 4,355,186 | 10/1982 | Becker et al. | 534/565 X |
| 4,355,189 | 10/1982 | Volkwein et al. | 534/565 |

FOREIGN PATENT DOCUMENTS

| | | | |
|---|---|---|---|
| 591380 | 1/1960 | Canada | 534/565 |
| 626965 | 9/1962 | Canada | 534/565 |

OTHER PUBLICATIONS

Encyclopedia of Chemical Technology vol. 2, p. 869, Second Edition.

*Primary Examiner*—Floyd D. Higel
*Attorney, Agent, or Firm*—Kevin T. Mansfield; Edward McC. Roberts

[57] ABSTRACT

Amines which are sparingly soluble in water are diazotised by first preparing a melt or solution of said amines and then precipitating them from the melt or a solution in an organic solvent by adding water, and then diazotising the resultant suspension. In this procedure, the reaction times are appreciably shorter than those of conventional processes.

12 Claims, No Drawings

PROCESS FOR THE DIAZOTISATION OF PRIMARY AROMATIC AMINES WHICH ARE SPARINGLY SOLUBLE IN WATER

This application is a continuation of application Ser. No. 803,710, filed 12-2-85 now abandoned.

The present invention relates to a process for the diazotisation of primary aromatic amines which are sparingly soluble in water.

The diazotisation of primary aromatic amines is carried out commercially on a large scale, especially in the production of azo dyes. However, the low solubility of amines which are sparingly soluble in water causes problems, so that in practice the amine is often converted into a finely particulate form by grinding. But even the suspensions of the amine so obtained react fairly slowly, especially at conventional diazotisation temperatures of 0°–30° C., preferably of 0°–5° C. The resultant diazonium salts decompose relatively easily. As the decomposition products adversely affect the quality of and azo dyes, long reaction times result in dyes of less than optimum purity.

It is the object of the present invention to eliminate, or at least to diminish, the shortcomings of the prior art processes referred to above for diazotising amines which are sparingly soluble in water.

This object is achieved by the process of this invention by precipitating the amine from a melt or solution thereof by mixing it with water and then diazotising the amine in the resulting suspension. Surprisingly, in this process it is possible to dispense with the complicated grinding procedure and still to add the diazotising agent much more rapidly without decomposition of the nitrite. The diazotisation time is appreciably shorter and the diazo compounds are obtained in the same, and often indeed in greater, purity than in the conventional process.

Accordingly, the present invention relates to a process for diazotising primary aromatic amines which are sparingly soluble in water, which comprises first preparing a melt or solution of the amine, precipitating the amine by mixing said melt or solution with water, and diazotising the resultant suspension of the amine by reaction with a commercially available diazotising agent in the temperature range from 10° C. for 0.1 to 20 minutes.

The diazotisation is preferably carried out adiabatically. The preferred temperature range is from 20° to 70° C., in particular 20° to 50° C.

In the context of this invention, an adiabatic reaction will be understood as meaning one in which the reaction mixture is neither cooled nor heated, with no reaction vessels employed which are specially insulated against heat transfer.

The diazotisation time depends, among other factors, on the nature of the amine and the temperature, and is preferably from 0.1 to 10 minutes.

Suitable solvents for the amine are water-soluble acids or water-soluble organic solvents.

Examples of suitable acids are sulfuric acid, phosphoric acid or acetic acid, and suitable organic solvents are e.g. compounds containing hydroxyl, carbonyl, carboxyl, sulfone or sulfonic acid groups, or polar aprotic compounds. Examples of suitable solvents are: methanol, ethanol, acetone, dimethylsulfoxide, sulfolane, sulfolene, dimethylformamide, tetramethylurea, N-methylpyrrolidone or acetonitrile. Mixtures of these organic solvents, or mixtures of the acids and organic solvents, may also be used.

It is preferred to use sulfuric acid, glacial acetic acid, dimethylsulfoxide, dimethylformamide, sulfolane, tetramethylurea or N-methylpyrrolidone.

The amine is conventionally dissolved at elevated temperature in the acid or the organic solvent, preferably in the temperature range from 30° and 150° C., most preferably from 50° to 100° C. If a melt of the amine is employed, said melt likewise has a temperature of 30° to 150° C., preferably of 50° to 100° C.

Suitable amines for the process of this invention are aromatic amines which are sparingly soluble in water. These amines are the diazo components, known from the chemistry of azo dyes, which are devoid of sulfo groups and are preferably derivatives of aniline, naphthylamine, or of heterocyclic aromatic amines. Examples of suitable amines are:

2-nitroaniline, 4-nitroaniline, 2-chloro-4,6-dinitroaniline, 4-nitro-1-naphthylamine, 4-chloro-1-naphthylamine, 2,5-dichloroaniline, 3,3'-dichlorobenzidine, 5-nitro-2-aminoanisole, 3-nitro-4-aminotoluene, 4-chloro-2-nitroaniline, 4-chloroaniline, 2,4-dichloroaniline, 3-nitro-4-aminoanisole, 2-chloro-4-nitro-aniline, 2-aminoanisole-4-sulfodiethylamide, 5-chloro-2-aminotoluene, 4-chloro-2-aminotoluene, 4-nitro-2-aminotoluene, 5-nitro-2-aminotoluene, 4-nitro-2-aminoanisole, 3,3'-dimethoxybenzidine, 3,3'-dimethyl-6,6'-dichlorobenzidine, 2-amino-4-chlorophenol, 2-aminophenol-4-sulfamide, 2-aminophenol-5-sulfamide, 2-aminophenol-4-sulfomethylamide, 3-amino-4-hydroxyphenylmethylsulfone, 2-amino-5-nitrophenylmethylsulfone, 4-amino-3-nitrophenylmethylsulfone, 2-(N-methyl-N-cyclohexylsulfonamide)aniline, 3-amino-1,2,4-triazole, 2-aminothiazole, 2-amino-4,2',4'-trichlorodiphenyl ether, 2-amino-6-methoxy-1,3-benzothiazole and 4-aminoazobenzene.

The process of this invention is particularly suitable for diazotising anilines which are substituted by one or more identical or different members selected from nitro, chloro and N,N-dialkylsulfonamido, where alkyl denotes straight chain, branched or cyclic $C_1$–$C_6$alkyl.

Particularly suitable amines for the process of the present invention are 2-chloro-4-nitroaniline, 4-chloro-2-nitroaniline and 2-(N-methyl-N-cyclohexylsulfonamido)aniline.

The melt or solution of the amine is mixed with water, preferably with ice or a mixture of ice and water, whereupon the amine precipitates almost completely. The water may be added to the melt or solution of the amine, but preferably the melt or solution of the amine is added to water or to a mixture of ice and water. The water may contain further auxiliaries, e.g. suitable surface-active agents and/or acid for the diazotisation. The water will preferably contain a mixture of a commercially available anionic and a nonionic surface-active agent, as well as acid in the total amount necessary for the diazotisation. If the amine has been dissolved in acid, then this amount of acid must of course be taken into account.

Suitable surface-active agents are the conventional anionic and/or anionic dispersants. Eligible nonionic dispersants are in particular condensates of alkylphenols and ethylene oxide; and eligible anionic dispersants are preferably condensates of aromatic sulfonic acids and formaldehyde. Preferred dispersants are condensates of $C_5$–$C_{15}$alkylphenols with 5 to 15 moles of ethylene oxide, preferably of $C_8$–$C_{12}$alkylphenols with 8 to 12 moles of ethylene oxide, as well as condensates of naphthalenesulfonic acids with formaldehyde, preferably of naphthalene-monosulfonic acids with formaldehyde.

All agents which cause nitrous acid to form in the reaction mixture may be used as diazotising agents, for example esters of nitrous acid or nitrosyl compounds such as nitrosylsulfuric acid or nitrosyl halides. It is preferred to use nitrites, in particular sodium nitrite, in conjunction with an acid, preferably a mineral acid.

The process of this invention may be carried out batchwise or preferably continuously. In the continuous process, a melt or solution of the amine is first prepared, the amine is precipitated by mixing said melt or solution with water, and the resultant suspension is reacted continuously with the diazotising agent while adding the required acid together with the amine suspension of from a separate feed line. It is also possible to mix the melt or solution of the amine and the acid direct with the solution of the nitrite, so that the amine is then partially diazotised without first being precipitated again.

Preferably the amine suspension and the solution of the nitrite are first introduced into a mixing chamber or a small stirred reactor in which the educts are thoroughly mixed and partial diazotisation takes place. The reaction mixture is then fed to a reactor, preferably a tubular reactor, where the reaction is brought to completion.

The process of this invention affords a solution of diazo components which contains only very little insoluble residue (amine) or even none at all.

A preferred embodiment of the process of the present invention comprises reacting the resultant solution of the diazo component continuously with a suitable coupling component, e.g. in a tubular reactor, while simultaneously further optional auxiliaries, e.g. bases for adjusting a less acid pH value, may be added.

The conditions of coupling are those conventionally employed and suitable coupling components are known compounds, preferably phenols, naphthols, anilines, naphthylamines, pyrazolones or acetoacetamides.

Compared with the identical azo dyes which are obtained in conventional manner, some of the azo dyes which are synthesized from the diazo components obtained by the process of this invention have greater purity, resulting in some cases in an improvement of the fastness properties of the dyeings obtained with said dyes.

The invention is illustrated by the following non-limitative Examples.

EXAMPLE 1

17.3 g of 2-chloro-4-nitroaniline are dissolved at 90° C. in 20 ml of glacial acetic acid and, with efficient stirring in a well-stirred small reactor, the solution is added to a mixture of 100 g of ice, 0.4 g of a mixture of an anionic and a nonionic dispersant (condensate of octylphenol and 8 moles of ethylene oxide and condensate of naphthalenesulfonic acid/formaldehyde) and 30 ml of concentrated HCl. The amine precipitates almost completely from the reaction mixture. Then 25 ml of 4N sodium nitrite solution are added to the reaction mixture at 20° C. over 18 seconds and stirring is continued for 1 minute. Diazotisation is substantially complete after this time. The reaction solution contains less than 1% of insoluble residue.

EXAMPLE 2

Comparison Example 17.3 g of 2-chloro-4-nitroaniline, 100 g of ice, 0.4 g of the dispersant mixture employed in Example 1, 30 ml of concentrated HCl and 20 ml of glacial acetic acid are suspended over 2 minutes in a well-stirred small reactor. Then 25 ml of 4N sodium nitrite solution are added at 20° C. over 2 minutes. A more rapid addition of the nitrite solution must be avoided, as it results in a marked decomposition of the nitrite. After stirring for 3½ minutes, a reaction solution of the same consistency as in Example 1 is obtained.

EXAMPLE 3

17.3 g of 2-chloro-4-nitroaniline are dissolved at 45° C. in 10 ml of dimethylsulfoxide and, with efficient stirring in a well-stirred small reactor, the solution is added to a mixture of 100 g of ice, 0.4 g of the mixture of an anionic and a nonionic dispersant employed in Example 1, and 30 ml of concentrated HCl. The amine precipitates almost completely from the reaction mixture. Then 25 ml of 4N sodium nitrite solution are added to the reaction mixture at 20° C. over 18 seconds and stirring is continued for 1 minute. Diazotisation is substantially complete after this time. The reaction solution contains less than 1% of insoluble residue.

EXAMPLE 4

17.3 g of 4-chloro-2-nitroaniline are dissolved at 90° C. in 20 ml of 96% sulfuric acid and, with efficient stirring in a well-stirred small reactor, the solution is added to a mixture of 100 g of ice, 0.4 g of the mixture of an anionic and a nonionic dispersant employed in Example 1, and 30 ml of concentrated HCl. The amine precipitates almost completely from the reaction mixture. Then 25 ml of 4N sodium nitrite solution are added to the reaction mixture at 20° C over 18 seconds and stirring is continued for 1 minute. Diazotisation is substantially complete after this time. The reaction solution contains less than 1% of insoluble residue.

EXAMPLE 5

Comparison Example 17.3 g of 4-chloro-2-nitroaniline, 100 g of ice, 0.4 g of the dispersant mixture employed in Example 1, 20 ml of 96% sulfuric acid are suspended over 2 minutes in a well-stirred small reactor. Then 25 ml of 4N sodium nitrite solution are added at 20° C. over 7 minutes. A more rapid addition of the nitrite solution must be avoided, as it results in a marked decomposition of the nitrite. After stirring for 8 minutes, a reaction solution of the same consistency as in Example 4 is obtained.

EXAMPLE 6

26.8 g of 2-(N-methyl-N-cyclohexylsulfonamido)aniline are dissolved at 80° C. in 20 ml of glacial acetic acid and, with efficient stirring in a well-stirred small reactor, the solution is added to a mixture of 100 g of ice, 0.4 g of the mixture of an anionic and a nonionic dispersant employed in Example 1, and 30 ml of concentrated HCl. The amine precipitates almost completely from the reaction mixture. Then 25 ml of 4N sodium nitrite solution are added to the reaction mixture at 20° C. over 1½ minutes and stirring is continued for 2 minutes. Diazotisation is substantially complete after this time. The reaction solution contains less than 1% of insoluble residue.

EXAMPLE 7

Comparison Example 26.8 g of 2-(N-methyl-N-cyclohexylsulfonylamido)aniline, 100 g of ice, 0.4 g of the dispersant mixture employed in Example 1, 30 ml of concentrated HCl and 20 ml of glacial acetic acid are suspended over 2 minutes in a well-stirred small reactor. Then 25 ml of 4N sodium nitrite solution are added at 20° C. over 6 minutes. A more rapid addition of the nitrite solution must be avoided, as it results in a marked decomposition of the nitrite. After stirring for 5 minutes, a reaction solution of the same consistency as in Example 6 is obtained.

EXAMPLE 8

173 g of 2-chloro-4-nitroaniline are dissolved at 85° C. in 200 ml of glacial acetic acid and the solution is then added, with efficient stirring in a well-stirred small reactor, to a mixture of 1000 ml of ice/water, 300 ml of concentrated hydrochloric acid, 2 g of the nonionic and 2 g of the anionic dispersant employed in Example 1. The amine precipitates in the form of a reactive suspension, which is then made up with water to a volume of 2000 ml. The temperature is about 20° C. This suspension is added continuously at a rate of 200 ml/min to a stirred reactor having a volume of about 100 ml and to which 4N sodium nitrite solution is fed continuously from a separate feed line at a rate of 25 ml/min. The reaction mixture flows from the stirred vessel through a tubular reactor which is 12 m long and has a diameter of 6 mm, and exits therefrom at a temperature of 27° C. in the form of a clear solution, thus indicating that the amine has been completely diazotised.

EXAMPLE 9

In a first storage flask, 865 g of 4-chloro-2-nitroaniline are dissolved at 85° C. in 1000 ml of 98% sulfuric acid. In a second storage flask, 1000 ml of 4N sodium nitrite solution are mixed with 5000 ml of ice/water. Through separate feed lines, 55.6 g/min of the amine solution and 150 ml/min of the nitrite solution are passed from the two storage flasks to a small stirred reactor of about 100 ml volume. The reaction mixture flows from the stirred reactor through a tubular reactor which is 12 m long and has a diameter of 6 mm, and exits therefrom at a temperature of ca. 30° C. in the form of a clear solution, thus indicating that the amine has been completely diazotised. The diazo solution is collected in an intermediate container, in which excess nitrite is destroyed with sulfamic acid.

In a separate flask, the solution of the coupling component is prepared by dissolving 910 g of 1-ethyl-3-cyano-4-methyl-6-hydroxypyrid-2-one and 60 g of sodium acetate in about 4000 ml of water with the addition of concentrated NaOH to adjust the pH to 7.5. The solution is then made up with water to a volume of 5000 ml.

Through separate feed lines, 197 ml/min of the diazo solution and 100 ml/min of the solution of the coupling component are fed at 30° C. to a continuously operating small reactor. The azo dye is obtained in over 98% yield after a residence time of <1 minute and at 30°–40° C.

What is claimed is:

1. A process for diazotizing weakly basic primary aromatic amines which are sparingly soluble in water, which comprises the steps of first preparaing a melt or solution of the amine in a water-soluble solvent at a temperature in the range from 30° C. to 150° C., precipitating said amine in the form of a reactive suspension consisting essentially of the free amine by adding said melt or solution to a stirred mixture of water, ice or a mixture thereof and an effective amount of a dispersant, and diazotizing said reactive suspension of the amine by reaction with a commercially available diazotizing agent in the temperature range from 10° to 100° C. for 0.1 to 20 minutes.

2. A process according to claim 1, wherein the diazotisation is carried out adiabatically in the temperature range from 20°–70° C.

3. A process according to claim 1, which comprises using a solution of the amine in a water-soluble acid or a water-soluble organic solvent.

4. A process according to claim 3, wherein sulfuric acid or glacial acetic acid is used as water-soluble acid.

5. A process according to claim 3, wherein the water-soluble solvent is dimethylsulfoxide, dimethylformamide, sulfolane, tetramethylurea or methylpyrrolidone.

6. A process according to claim 1, wherein the amine is a derivative of aniline, naphthylamine or of a heterocyclic amine.

7. A process according to claim 6, which comprises using an aniline which is substituted by one or more of the same or different members selected from nitro, chloro and N,N-dialkylsulfonamido.

8. A process according to claim 7, wherein the aniline is 2-chloro-4-nitroaniline, 4-chloro-2-nitroaniline or 2-(N-methyl-N-cyclohexylsulfonamido)aniline.

9. A process according to claim 1, wherein as dispersant a mixture of an anionic and a nonionic surface-active agent is used.

10. A process according to claim 9, which comprises the use of a condensate of a $C_8$–$C_{12}$alkylphenol with 8 to 12 moles of ethylene oxide and a condensate of a naphthalene-monosulfonic acid and formaldehyde.

11. A process according to claim 1, which comprises preparing a melt or solution of the amine, precipitating said amine by mixing said solution or melt with water, ice or a mixture thereof, and continuously reacting the resultant suspension with a diazotizing agent.

12. A process according to claim 11, which comprises mixing the suspension of the amine continuously in a mixing chamber with the diazotising agent, subsequently feeding the reaction mixture to a reactor, and bringing the reaction to completion therein.

* * * * *